United States Patent
Suzuki et al.

(10) Patent No.: US 9,333,266 B2
(45) Date of Patent: May 10, 2016

(54) MEDICINAL AGENT FOR MEDICAL APPLICATIONS

(75) Inventors: Minako Suzuki, Tokyo (JP); Taka Nakahara, Tokyo (JP); Hiroshi Ishikawa, Tokyo (JP); Akihiro Oyama, Tokyo (JP)

(73) Assignees: THE NIPPON DENTAL UNIVERSITY, Tokyo (JP); HITACHI ALOKA MEDICAL, LTD., Tokyo (JP)

( * ) Notice: Subject to any disclaimer, the term of this patent is extended or adjusted under 35 U.S.C. 154(b) by 25 days.

(21) Appl. No.: 14/131,613

(22) PCT Filed: Aug. 9, 2012

(86) PCT No.: PCT/JP2012/070291
§ 371 (c)(1),
(2), (4) Date: Jan. 8, 2014

(87) PCT Pub. No.: WO2013/022052
PCT Pub. Date: Feb. 14, 2013

(65) Prior Publication Data
US 2014/0171629 A1 Jun. 19, 2014

(30) Foreign Application Priority Data
Aug. 11, 2011 (JP) .................................. 2011-176303

(51) Int. Cl.
*A61K 47/48* (2006.01)
*G01N 33/50* (2006.01)
*A61K 49/04* (2006.01)
*B82Y 5/00* (2011.01)

(52) U.S. Cl.
CPC ..... *A61K 47/48061* (2013.01); *A61K 47/48023* (2013.01); *A61K 49/0423* (2013.01); *B82Y 5/00* (2013.01); *G01N 33/5008* (2013.01)

(58) Field of Classification Search
CPC .................... G01N 33/5008; A61K 47/48023; A61K 47/48061; B82Y 5/00
USPC .................... 536/6.4; 548/402, 403, 414, 468
See application file for complete search history.

(56) References Cited

U.S. PATENT DOCUMENTS

| | | | |
|---|---|---|---|
| 6,822,086 B1 | 11/2004 | Papisov | |
| 6,844,319 B1 | 1/2005 | Poelstra et al. | |
| 2004/0167061 A1* | 8/2004 | Faulk | A61K 47/483 514/1.3 |
| 2004/0171067 A1 | 9/2004 | Hinuma et al. | |
| 2004/0220384 A1 | 11/2004 | Hinuma et al. | |
| 2005/0202075 A1 | 9/2005 | Pardridge et al. | |
| 2008/0206146 A1 | 8/2008 | Akhtari et al. | |
| 2009/0004118 A1 | 1/2009 | Nie et al. | |
| 2009/0053302 A1 | 2/2009 | Boulikas | |
| 2009/0156657 A1* | 6/2009 | Naito et al. | 514/415 |
| 2009/0286760 A1 | 11/2009 | Chen | |
| 2010/0209347 A1 | 8/2010 | Hattori | |

FOREIGN PATENT DOCUMENTS

| | | |
|---|---|---|
| JP | 2002-532384 A | 10/2002 |
| JP | 2003-506417 A | 2/2003 |
| JP | 2003-315332 A | 11/2003 |
| JP | 2007-528899 A | 10/2007 |
| JP | 2008-515915 A | 5/2008 |
| JP | 2008-533203 A | 8/2008 |
| JP | 2009-528340 A | 8/2009 |
| WO | 2009/041666 A1 | 4/2009 |

OTHER PUBLICATIONS

Ferrari et al. Rhabdomyosarcoma in Adults. Cancer 98:571-80, 2003.*
International Search Report dated Sep. 11, 2012 issued in corresponding application No. PCT/JP2012/070291.
Notice of Grounds for Rejection dated Sep. 4, 2012 issued in application No. JP2011-176303.
Notice of Grounds for Rejection dated Jul. 30, 2013 issued in application No. JP2011-176303.
Nagai, Excerpt from "New Drug Delivery Systems", Jan. 31, 2000, pp. 169-170.
Ohi, "Characterization, anticancer drug susceptibility and atRA-induced growth inhibition of a novel cell line (HUMEMS) established from pleural effusion of alveolar rhabdomyosarcoma of breast tissue", Human Cell, vol. 20, 2007, pp. 39-51.
Suzuki et al., "Establishment and characterization of the rhabdomyosarcoma cell line designated NUTOS derived from the human tongue sarcoma: Special reference to the susceptibility of anti-cancer drugs", Human Cell, vol. 23, 2010, pp. 65-73.
Notification of Transmittal of Translation of the International Preliminary Report on Patentability dated Feb. 20, 2014 of PCT/JP2012/070291, form PCT/IB/338 and form PCT/IPEA/409 (5 pages).
Extended European Search Report dated Feb. 9, 2015, issued in corresponding European Application No. 12822760.0. (8 pages).
Jacobs, S. et al. Phase II Trial of Ixabepilone Administered Daily for Five Days in Children and Young Adults with Refractory Solid Tumors: A Report from the Children's Oncology Group. Jan. 12, 2010. pp. 750-755.
Maki, R et al., "Randomized Phase II Study of Gemcitabine and Docetaxel Compared With Gemcitabine Alone in Patients With Metastatic Soft Tissue Sarcomas: Results of Sarcoma Alliance for Research Through Collaboration Study 002," Journal of Clinical Oncology, vol., 25, No. 19, Jul. 1, 2007, pp. 2755-3790.

* cited by examiner

*Primary Examiner* — Clinton Brooks
*Assistant Examiner* — Yih-Horng Shiao
(74) *Attorney, Agent, or Firm* — Westerman, Hattori, Daniels & Adrian, LLP

(57) ABSTRACT

Provided is a medicinal agent for medical applications, which can act on the function of a target cell specifically. The medicinal agent for medical applications comprises: a cell-incorporated substance that can be incorporated into a target cell specifically; and an acting substance that can act on the function of the target cell and is bound to the cell-incorporated substance.

6 Claims, 5 Drawing Sheets

MEDICINAL AGENT FOR MEDICAL APPLICATIONS

TECHNICAL FIELD

The present invention relates to a medicinal agent for medical applications to be used in a drug delivery system, etc., and a method for searching for a novel medicinal agent.

BACKGROUND ART

An anticancer agent goes through the whole body via the bloodstream when it is administered to a patient, and damages not only cancer tissues in which the cell proliferation is active, but also normal cells whose proliferation is active, such as normal small-intestinal mucosa, bone marrow, or hair root cells, and therefore, side effects occur in some cases.

In order to suppress the side effects, a drug targeting therapy in which an anticancer agent can specifically act on cancer tissues, a so-called drug delivery system (DDS), has been contemplated. As one of the methods, there is a method in which a cancer-specific antibody is bound to an anticancer substance or the like, and the anticancer substance is specifically accumulated in cancer tissues. However, with this method, even if the anticancer substance is accumulated on the cancer tissue surface, the anticancer substance is bound to a large antibody, and therefore, the anticancer substance is unlikely to be incorporated into cancer cells and its effect is limited. The development of not only an anticancer agent, but also a medicinal agent which has a high desired effect but less side effects has been in demand.

On the other hand, a rhabdomyosarcoma is a malignant soft tissue tumor, which is found in children and young people, and in which cells differentiating into striated muscle undergo malignant transformation, with the following three histopathological types: embryonal rhabdomyosarcoma, pleomorphic rhabdomyosarcoma, and alveolar rhabdomyosarcoma have been reported. Such a rhabdomyosarcoma responds poorly to chemotherapy, and particularly, the malignancy of alveolar rhabdomyosarcoma is high, and there has been a demand to establish a treatment method therefor. It has been reported that this rhabdomyosarcoma incorporates serotonin (see NPL 1 and NPL 2).

CITATION LIST

Non Patent Literature

NPL 1: Ohi S., Characterization, anticancer drug susceptibility and atRA-induced growth inhibition of a novel cell line (HUMEMS) established from pleural effusion of alveolar rhabdomyosarcoma of breast tissue., Hum Cell, 2007; 20: page 39-51.

NPL 2: Minako SUZUKI et al., Establishment and characterization of the rhabdomyosarcoma cell line designated NUTOS derived from the human tongue sarcoma: Special reference to the susceptibility of anti-cancer drugs, Hum Cell, 2010; 23: page 65-73.

SUMMARY OF INVENTION

Technical Problems

An object of the present invention is to provide a medicinal agent for medical applications which can specifically act on the function of a target cell, and a method for searching for a novel medicinal agent.

Solution to Problems

The present invention is directed to a medicinal agent for medical applications including: a cell-incorporated substance that can specifically be incorporated into a target cell; and an acting substance that can act on the function of the target cell and is bound to the cell-incorporated substance.

Further, in the medicinal agent for medical applications, it is preferred that the target cell is a rhabdomyosarcoma-derived cell, and the cell-incorporated substance is serotonin.

Still further, in the medicinal agent for medical applications, it is preferred that the acting substance is an anticancer substance for a rhabdomyosarcoma.

Further, the present invention is directed to a method for searching for a novel medicinal agent, including: a cell-incorporated substance selection step in which a cell-incorporated substance that can specifically be incorporated into a target cell is selected; and a cell-incorporated substance-acting substance binding step in which an acting substance that can act on the function of the target cell is bound to the selected cell-incorporated substance, thereby obtaining a cell-incorporated substance-acting substance conjugate medicinal agent.

Further, in the method for searching for a novel medicinal agent, it is preferred that the cell-incorporated substance selection step includes: a mixing step in which the target cell and a culture medium containing at least one chemical substance are mixed with each other; and a reduced chemical substance specification step in which a chemical substance whose amount is reduced after the lapse of a predetermined time is specified among the at least one chemical substance contained in the culture medium, and the chemical substance whose amount is reduced is selected as the cell-incorporated substance that can specifically be incorporated into the target cell.

Advantageous Effects of Invention

According to the present invention, a medicinal agent for medical applications which can specifically act on the function of a target cell can be provided by binding an acting substance that can act on the function of the target cell to a cell-incorporated substance that can specifically be incorporated into the target cell.

Further, a novel medicinal agent that can specifically act on the function of a target cell can be searched for by a simple method by selecting a cell-incorporated substance that can specifically be incorporated into a target cell, and binding an acting substance that can act on the function of the target cell to the selected cell-incorporated substance, thereby obtaining a cell-incorporated substance-acting substance conjugate medicinal agent.

DESCRIPTION OF EMBODIMENTS

Figure 1:
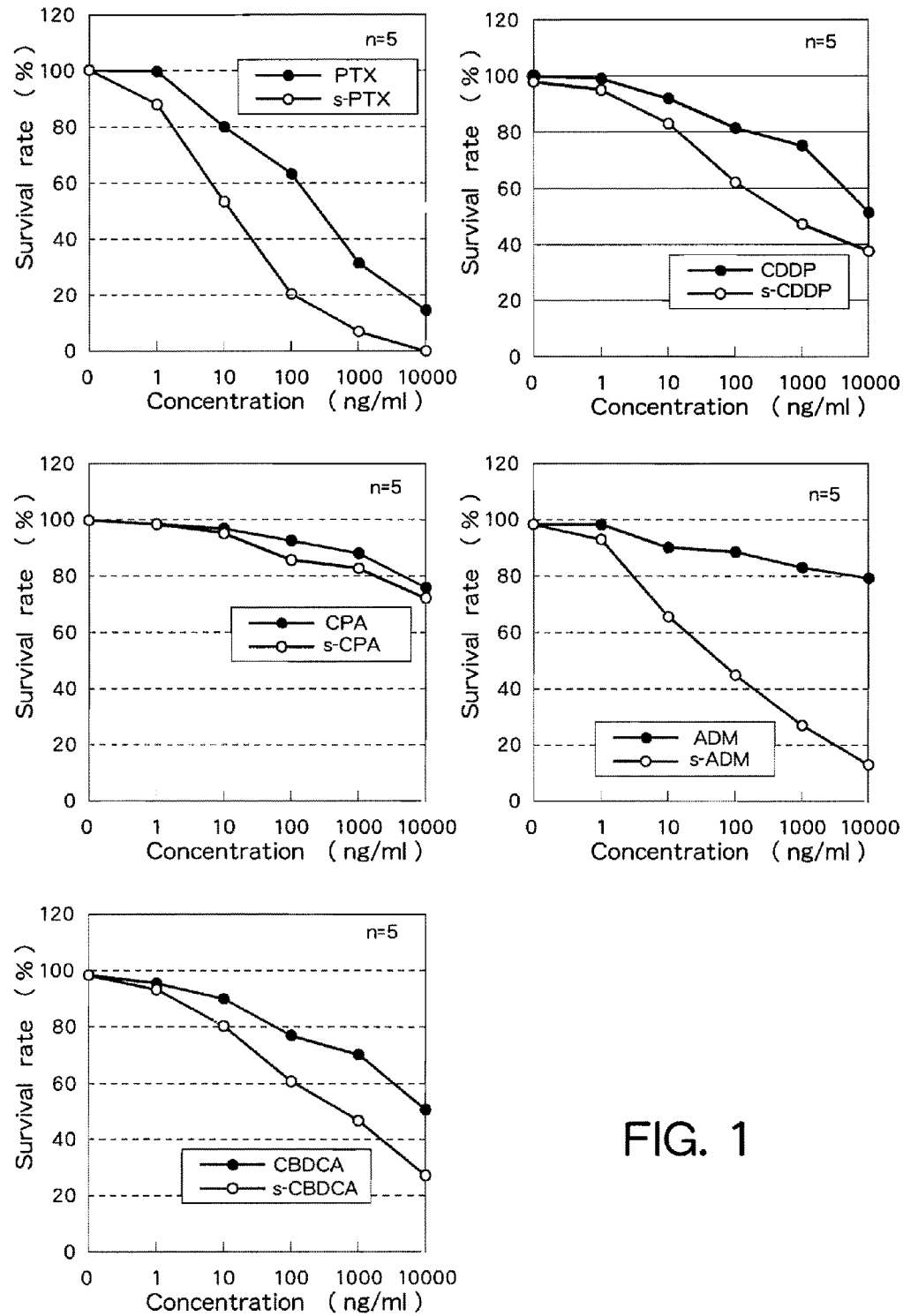
FIG. 1 shows graphs, each of which indicates a relationship between the concentration (ng/ml) of an added anticancer agent and the survival rate (%) of cells after 15 hours in Example 7 according to the present invention and Comparative Example 1.

Hereinafter, an embodiment of the present invention will be described. This embodiment is an example of implementing the present invention, and the present invention is not limited to this embodiment.

<Medicinal Agent for Medical Applications>

The medicinal agent for medical applications according to an embodiment of the present invention is a cell-incorporated substance-acting substance conjugate medicinal agent in which an acting substance that can act on the function of a target cell is bound to a cell-incorporated substance that can specifically be incorporated into the target cell.

For example, since a rhabdomyosarcoma can specifically incorporate serotonin, if an anticancer substance, a bioactivity inhibiting substance, or the like is bound to serotonin so that such a substance can specifically be incorporated into a rhabdomyosarcoma, a drug delivery system (DDS) whose target is narrowed down to a rhabdomyosarcoma can be achieved.

The cell-incorporated substance-acting substance conjugate medicinal agent such as a serotonin-anticancer substance conjugate medicinal agent in which an anticancer substance is bound to serotonin can specifically be incorporated into the target cell such as a rhabdomyosarcoma, and therefore can specifically act on the function of the target cell. Since the cell-incorporated substance-acting substance conjugate medicinal agent such as a serotonin-anticancer substance conjugate medicinal agent can specifically be incorporated into the target cell such as a rhabdomyosarcoma, side effects can be suppressed. In addition, the cell-incorporated substance-acting substance conjugate medicinal agent such as a serotonin-anticancer substance conjugate medicinal agent can be made quite small compared with antibodies, and therefore can easily be incorporated into the target cell.

Examples of the target cell include cancer cells, sarcoma cells, and normal cells. Examples of the cancer cells include stomach cancer, lung cancer, breast cancer, kidney cancer, thyroid cancer, liver cancer, pancreatic cancer, bladder cancer, and neuronal cancer cells; examples of the sarcoma cells include tumor cells derived from sarcomas such as rhabdomyosarcoma, leiomyosarcoma, osteosarcoma, and liposarcoma; and examples of the normal cells include bone marrow, neuronal cells, muscle cells, and endocrine cells.

Examples of the cell-incorporated substance that can specifically be incorporated into a target cell include serotonin (5-hydroxytryptamine) that can specifically be incorporated into a rhabdomyosarcoma-derived tumor cell, steroid that can specifically be incorporated into a muscle-derived cell, and vitamin A that can specifically be incorporated into a retina-derived cell. The cell-incorporated substance that can specifically be incorporated into a target cell can be selected by a cell-incorporated substance selection step in a method for searching for a novel medicinal agent described below.

Examples of the acting substance that can act on the function of a target cell include an anticancer substance that can act on cancer cells, a cytokine that can act on cell differentiation, a hormonal substance that can act on homeostasis or the like.

Here, the phrase "that can act on the function" of a target cell refers to an action including an action of suppressing the function, an action of promoting the function, and an action of maintaining the function.

Examples of the anticancer substance include paclitaxel (PTX, also known as Taxol (TXL)), cisplatin (CDDP, also known as Briplatin), carboplatin (CBDCA), adriamycin (ADM), cyclophosphamide (CPA) and the like.

The phrase "that can specifically be incorporated into a target cell" as used herein means that it can specifically (selectively) be incorporated into a target cell among a plurality of (at least two) cells.

Specific examples of the medicinal agent for medical applications according to the embodiment of the present invention include an agent in which an anticancer substance that can act on a rhabdomyosarcoma is bound to serotonin that can specifically be incorporated into a rhabdomyosarcoma-derived cancer cell. Serotonin is a type of hormone present in the body and is a substance with almost no toxicity, and therefore, a highly safe serotonin-acting substance conjugate medicinal agent can be provided.

The serotonin-acting substance conjugate medicinal agent such as a serotonin-anticancer substance conjugate medicinal agent can be applied not only to a rhabdomyosarcoma-derived cancer cell, but also to a cell that can specifically incorporate serotonin or a part of the structure of serotonin as a target cell.

Examples of the bond between the cell-incorporated substance that can specifically be incorporated into a target cell and the acting substance that can act on the function of the target cell include chemical bonds such as a covalent bond, a coordinate bond, an ionic bond, and a hydrogen bond, but there is no particular restriction. Among these, a covalent bond is preferred from the viewpoint of stability and the like.

As a method for binding the acting substance that can act on the function of a target cell to the cell-incorporated substance that can specifically be incorporated into the target cell, a common chemical synthetic method such as organic synthesis can be used. For example, a cell-incorporated substance such as serotonin and an anticancer substance can be bound to each other by being mixed in an aqueous solvent such as physiological saline or phosphate-buffered saline (PBS), which is controlled to have a near neutral pH (pH 6.0 to 8.0), and reacted with each other. The reaction temperature, the reaction time, and so on may be determined appropriately. Incidentally, the number of binding sites between the cell-incorporated substance and the anticancer substance is not limited to one, and the cell-incorporated substance-acting substance conjugate medicinal agent may be a mixture of substances in which the binding can be achieved at a plurality of reaction sites. For example, in the case of adriamycin (ADM), which is an anticancer substance, and serotonin serving as the cell-incorporated substance, it is considered that a portion indicated by the arrow in the following structural formula of adriamycin can be reacted with the amino group of serotonin, but the reaction site is not limited to the following portion indicated by the arrow.

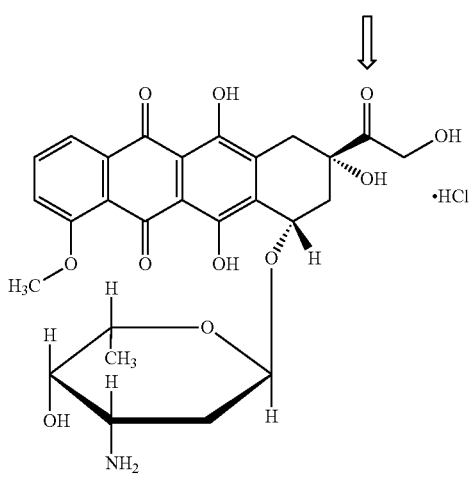

The medicinal agent for medical applications (cell-incorporated substance-acting substance conjugate medicinal agent) according to the embodiment of the present invention can be applied to, other than a drug delivery system (DDS), for example, enhancement of absorption of a drug, prolongation of life span of a drug, controlled-release of a drug, and so on.

<Method for Searching for Novel Medicinal Agent>

The method for searching for a novel medicinal agent according to an embodiment of the present invention includes a cell-incorporated substance selection step in which a cell-incorporated substance that can specifically be incorporated into a target cell is selected; and a cell-incorporated substance-acting substance binding step in which an acting substance that can act on the function of the target cell is bound to the selected cell-incorporated substance, thereby obtaining a cell-incorporated substance-acting substance conjugate medicinal agent.

The cell-incorporated substance selection step includes, for example: a mixing step in which the target cell and a culture medium containing at least one chemical substance are mixed with each other; and a reduced chemical substance specification step in which a chemical substance whose amount is reduced after the lapse of a predetermined time is specified among the at least one chemical substance contained in the culture medium, and in the cell-incorporated substance selection step, the chemical substance whose amount is reduced is selected as the cell-incorporated substance that can specifically be incorporated into the target cell.

In the mixing step, as the culture medium, a medium obtained by mixing at least one arbitrary chemical substance in a cell culture medium to be commonly used for cell culture may be used. As the culturing conditions, culturing conditions to be commonly used for cell culture may be used.

In the reduced chemical substance specification step, as a method for specifying a chemical substance whose amount is reduced, for example, a high performance liquid chromatography (HPLC) method, a gas chromatography (GC) method, a mass spectrometry method, etc., and a combination thereof can be used.

Examples of the bond between the selected cell-incorporated substance and the acting substance that can act on the function of the target cell to be formed in the cell-incorporated substance-acting substance binding step include chemical bonds such as a covalent bond, a coordinate bond, an ionic bond, and a hydrogen bond as described above, but there is no particular restriction.

In the cell-incorporated substance-acting substance binding step, as a method for binding the selected cell-incorporated substance and the acting substance that can act on the function of the target cell, as described above, a common chemical synthetic method such as organic synthesis can be used.

According to such a method for searching for a novel medicinal agent, a candidate for a novel medicinal agent that can specifically act on the function of a target cell and can be used for a drug delivery system (DDS) whose target is narrowed down to a specific target cell, enhancement of absorption of a drug, prolongation of life span of a drug, controlled-release of a drug, and so on can be searched for by a simple method.

EXAMPLES

Hereinafter, the present invention will be more specifically described in detail with reference to Examples and Comparative Examples. However, the present invention is not limited to the following Examples.

From alveolar rhabdomyosarcoma developed in the tongue of a 17-year-old Japanese girl, a rhabdomyosarcoma cell line (NUTOS: Accession No. NITE AP-1394) was established. There has been no report on a rhabdomyosarcoma developed in the tongue so far. The NUTOS cell line is a very useful cell line for studying the treatment of a rhabdomyosarcoma.

Example 1

Incorporation of Serotonin into NUTOS Cells

When fetal bovine serum containing serotonin was added to a culture medium containing this NUTOS cell line, the amount of serotonin in the culture medium was decreased. Further, it was found that serotonin in the fetal bovine serum added to the culture medium was specifically incorporated into the NUTOS cells based on the phenomenon that the cell emitted light by an anti-serotonin antibody in immunostaining and when the serum in the culture medium was blocked by the anti-serotonin antibody, the cells did not emit light, etc. The detailed mechanism of this incorporation has not been elucidated yet, and also the role of serotonin incorporated therein has not been elucidated yet.

Synthesis of Serotonin-Anticancer Substance Conjugate Medicinal Agent

Example 2

Synthesis of Serotonin-Paclitaxel (PTX) Conjugate Medicinal Agent

Serotonin and paclitaxel (PTX), which is an anticancer substance, were mixed in phosphate-buffered saline (PBS), which was controlled to have a near neutral pH (pH 6.0 to 8.0), and reacted with each other, whereby a serotonin-paclitaxel (PTX) conjugate medicinal agent (hereinafter referred to as "s-PTX") was synthesized.

Example 3

Synthesis of Serotonin-Cisplatin (CDDP) Conjugate Medicinal Agent

A serotonin-cisplatin (CDDP) conjugate medicinal agent (hereinafter referred to as "s-CDDP") was synthesized in the same manner as in Example 2.

Example 4

Synthesis of Serotonin-Carboplatin (CBDCA) Conjugate Medicinal Agent

A serotonin-carboplatin (CBDCA) conjugate medicinal agent (hereinafter referred to as "s-CBDCA") was synthesized in the same manner as in Example 2.

Example 5

Synthesis of Serotonin-Adriamycin (ADM) Conjugate Medicinal Agent

A serotonin-adriamycin (ADM) conjugate medicinal agent (hereinafter referred to as "s-ADM") was synthesized in the same manner as in Example 2.

Example 6

Synthesis of Serotonin-Cyclophosphamide (CPA) Conjugate Medicinal Agent

A serotonin-cyclophosphamide (CPA) conjugate medicinal agent (hereinafter referred to as "s-CPA") was synthesized in the same manner as in Example 2.

Example 7

A rhabdomyosarcoma cell line (NUTOS) established from alveolar rhabdomyosarcoma developed in the tongue of a 17-year-old Japanese girl was used. According to the following procedure, s-PTX, s-CDDP, s-CBDCA, s-ADM, and s-CPA synthesized in Examples 2 to 6 were added to confluent cells (NUTOS), as an anticancer agent, and the percentage of incorporation of a dye after 15 hours was counted. The results are shown in FIGS. 1(a) to 1(e). In FIG. 1, the horizontal axis represents the concentration (ng/ml) of the added anticancer agent and the longitudinal axis represents the survival rate (%) of the cells after 15 hours (n=5).

(Experimental Procedure)
1. Cells were plated on a plate and cultured to a confluent state using a DMEM/F12 culture medium supplemented with 15% fetal bovine serum.
2. The culture medium was removed and replaced with a serum-free DMEM/F12 culture medium supplemented with a given amount of an anticancer agent, and the cells were cultured for 15 hours.
3. The culture medium was removed, and the cells were washed with Hanks' solution and detached with trypsin. The detached cells were transferred to a tube and centrifuged.
4. The supernatant was removed, and the cells were suspended in a given amount of a culture medium.
5. An aliquot of the cell suspension was taken and the same amount of trypan blue was added thereto. Then, the cells were counted using a hemocytometer.

Comparative Example 1

The percentage of incorporation of a dye was counted 15 hours after adding an anticancer agent to confluent cells (NU-TOS) in the same manner as in Example 7, except that paclitaxel (PTX), cisplatin (CDDP), carboplatin (CBDCA), adriamycin (ADM), and cyclophosphamide (CPA) were used as the anticancer agent in place of s-PTX, s-CDDP, s-CBDCA, s-ADM, and s-CPA. The results are shown in FIG. 1.

PTX (FIG. 1(a)) and CDDP (FIG. 1(b)) each exhibited an anticancer effect by itself. However, a stronger anticancer effect was exhibited in the case where PTX or CDDP was bound to serotonin (s-PTX or s-CDDP). Similarly, CBDCA (FIG. 1(e)) also exhibited an anticancer effect by itself, but, a stronger anticancer effect was exhibited in the case where CBDCA was bound to serotonin (s-CBDCA). ADM (FIG. 1(d)) exhibited only a slight anticancer effect by itself, but a dramatically stronger effect was exhibited in the case where ADM was bound to serotonin (s-ADM). CPA (FIG. 1(c)) exhibited only a slight anticancer effect by itself, but a somewhat stronger effect was exhibited in the case where CPA was bound to serotonin (s-CPA).

Example 8 and Comparative Example 2

Figure 2:
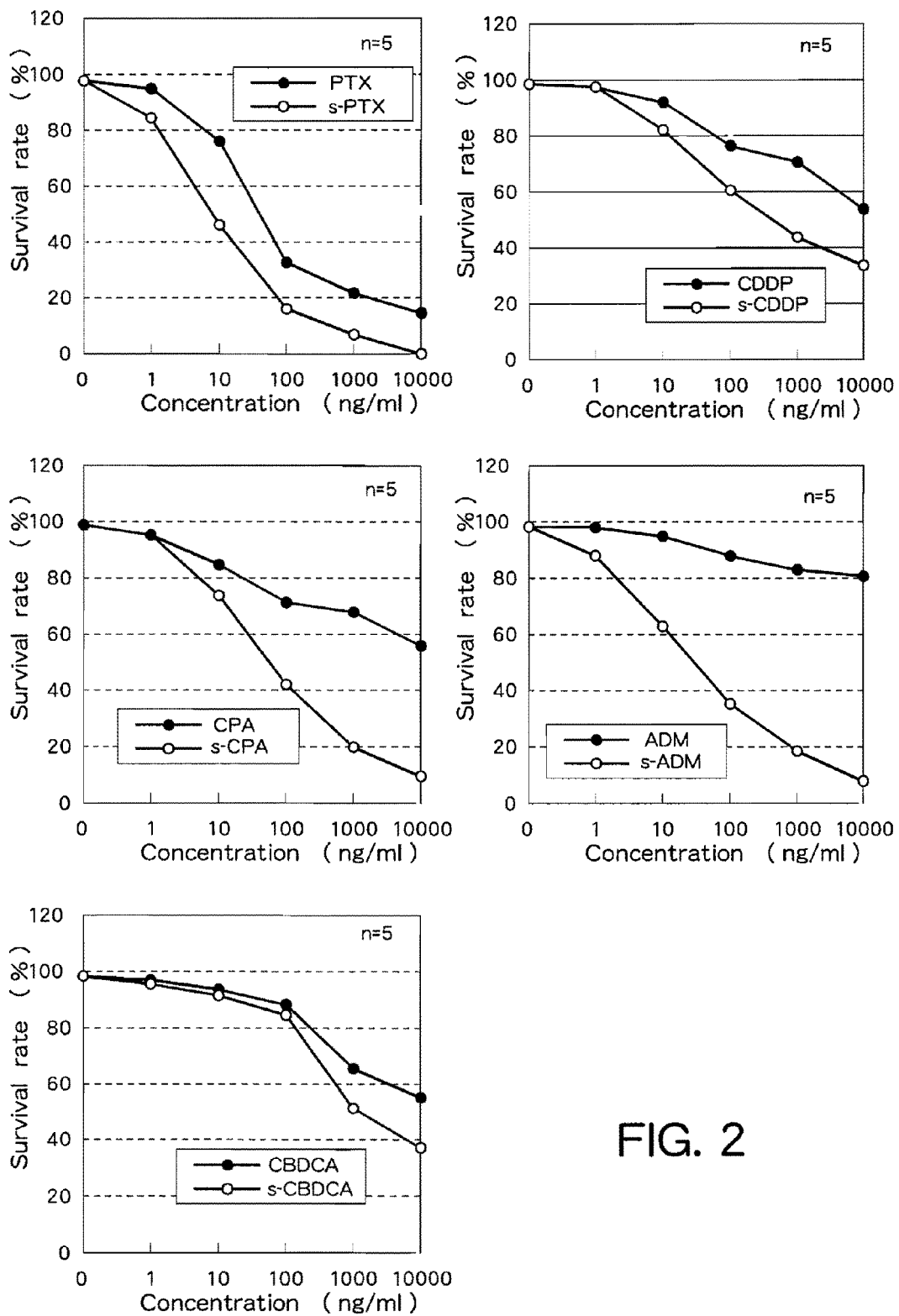
FIG. 2 shows graphs, each of which indicates a relationship between the concentration (ng/ml) of an added anticancer agent and the survival rate (%) of cells after 15 hours in Example 8 according to the present invention and Comparative Example 2.

The percentage of incorporation of a dye was counted 15 hours after adding an anticancer agent (s-PTX, s-CDDP, s-CBDCA, s-ADM, or s-CPA (all of which are in Example 8), PTX, CDDP, CBDCA, ADM, or CPA (all of which are in Comparative Example 2)) to confluent cells (HUMENS) in the same manner as in Example 7 or Comparative Example 1, except that a rhabdomyosarcoma cell line (HUMENS) established from alveolar rhabdomyosarcoma obtained from the mammary gland was used as the cells in place of NUTOS. The results are shown in FIG. 2.

PTX (FIG. 2(a)) and CDDP (FIG. 2(b)) each exhibited an anticancer effect by itself, but a stronger anticancer effect was exhibited in the case where PTX or CDDP was bound to serotonin (s-PTX or s-CDDP). Similarly, CBDCA (FIG. 2(e)) also exhibited an anticancer effect by itself, but a stronger anticancer effect was exhibited in the case where CBDCA was bound to serotonin (s-CBDCA). ADM (FIG. 2(d)) exhibited only a slight anticancer effect by itself, but a dramatically stronger effect was exhibited in the case where ADM was bound to serotonin (s-ADM). CPA (FIG. 2(c)) exhibited an anticancer effect by itself, but a dramatically stronger effect was exhibited in the case where CPA was bound to serotonin (s-CPA).

Comparative Example 3

Figure 3:
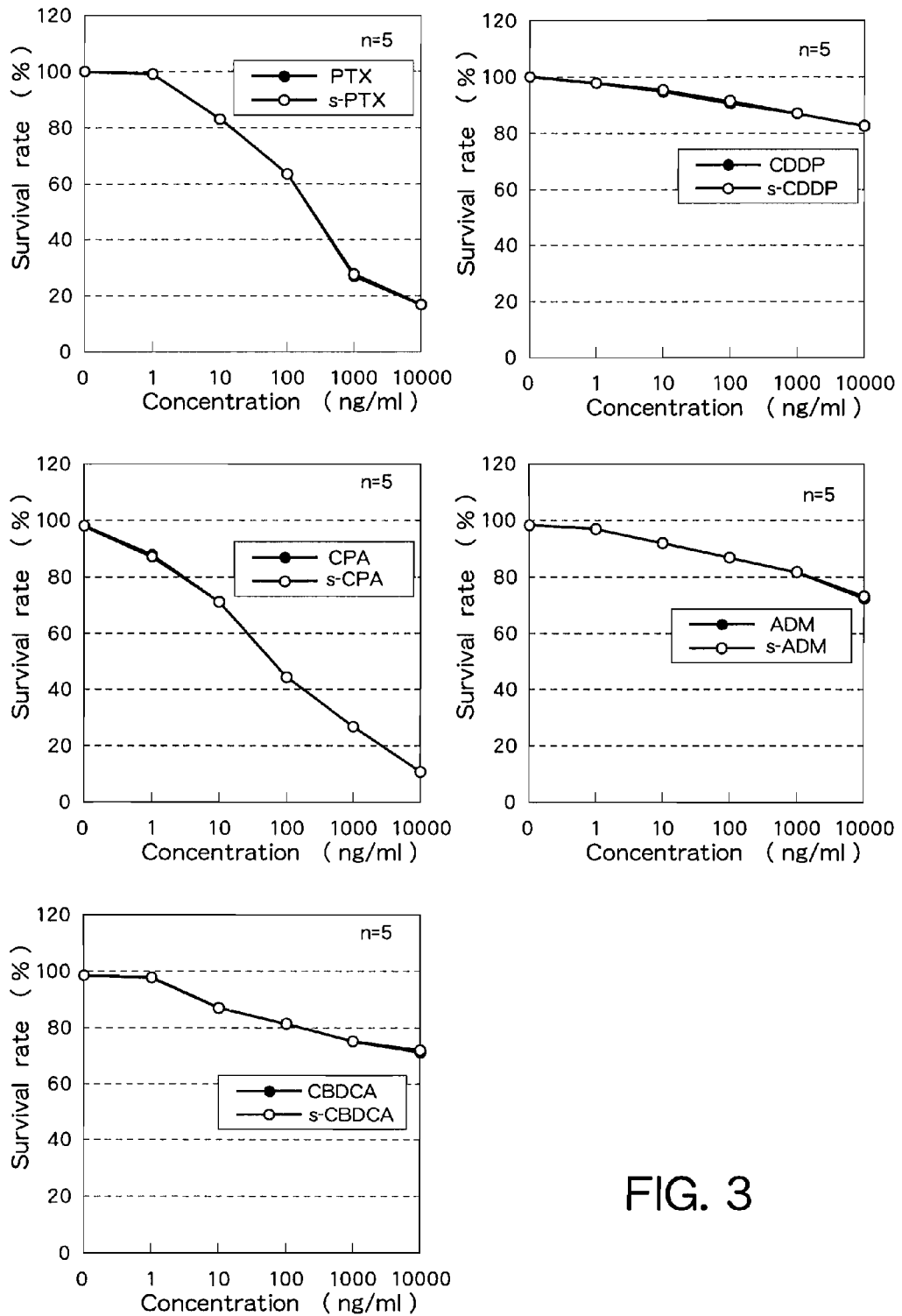
FIG. 3 shows graphs, each of which indicates a relationship between the concentration (ng/ml) of an added anticancer agent and the survival rate (%) of cells after 15 hours in Comparative Example 3.

The percentage of incorporation of a dye was counted 15 hours after adding an anticancer agent (s-PTX, s-CDDP, s-CBDCA, s-ADM, s-CPA, PTX, CDDP, CBDCA, ADM, or CPA) to confluent cells (endometrial cancer cells) in the same manner as in Example 7 or Comparative Example 1, except that endometrial cancer cells were used as the cells in place of NUTOS. The results are shown in FIG. 3.

Comparative Example 4

Figure 4:
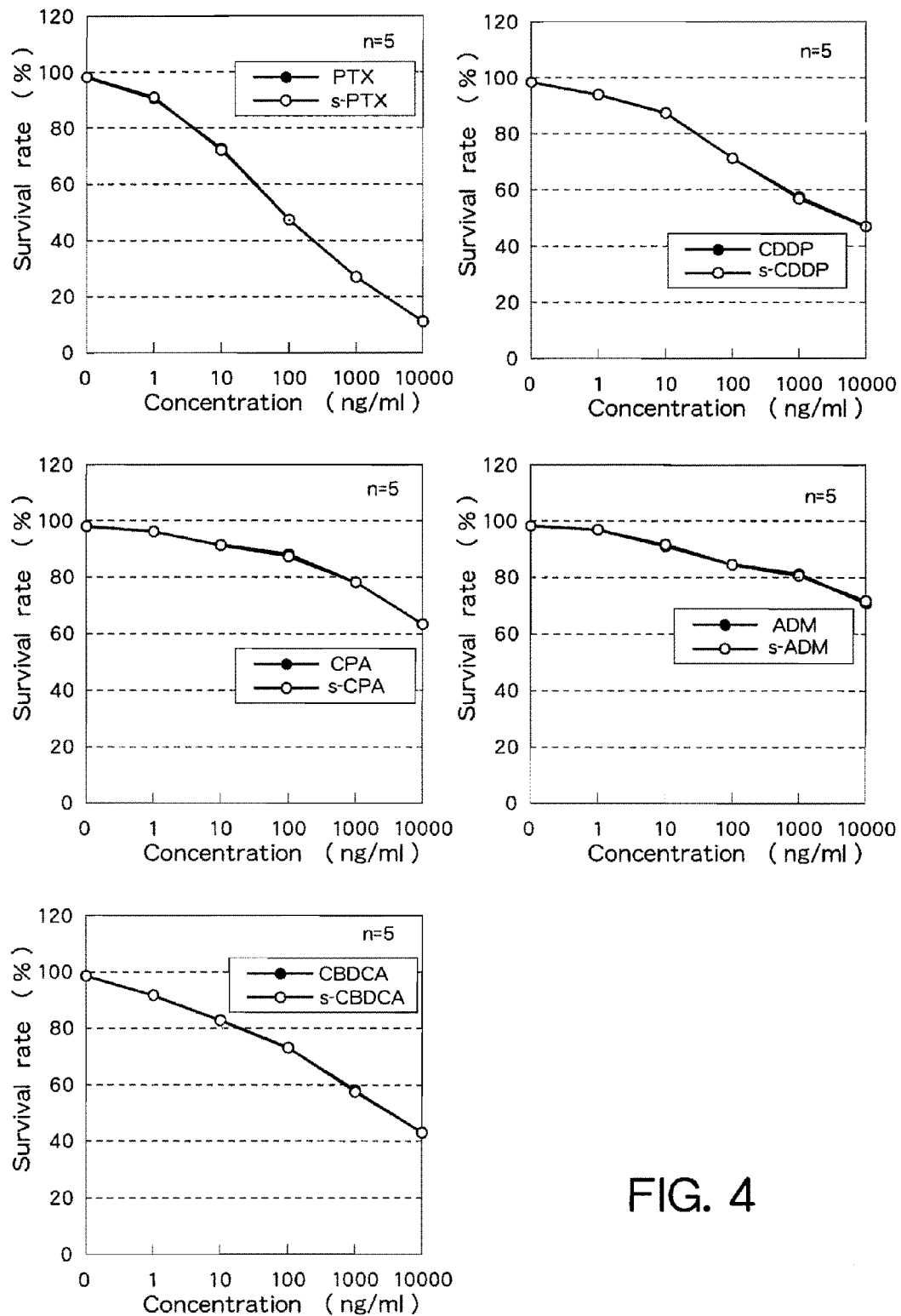
FIG. 4 shows graphs, each of which indicates a relationship between the concentration (ng/ml) of an added anticancer agent and the survival rate (%) of cells after 15 hours in Comparative Example 4.

The percentage of incorporation of a dye was counted 15 hours after adding an anticancer agent (s-PTX, s-CDDP, s-CBDCA, s-ADM, s-CPA, PTX, CDDP, CBDCA, ADM, or CPA) to confluent cells (ovarian cancer cells) in the same manner as in Example 7 or Comparative Example 1, except that ovarian cancer cells were used as the cells in place of NUTOS. The results are shown in FIG. 4.

Comparative Example 5

Figure 5:
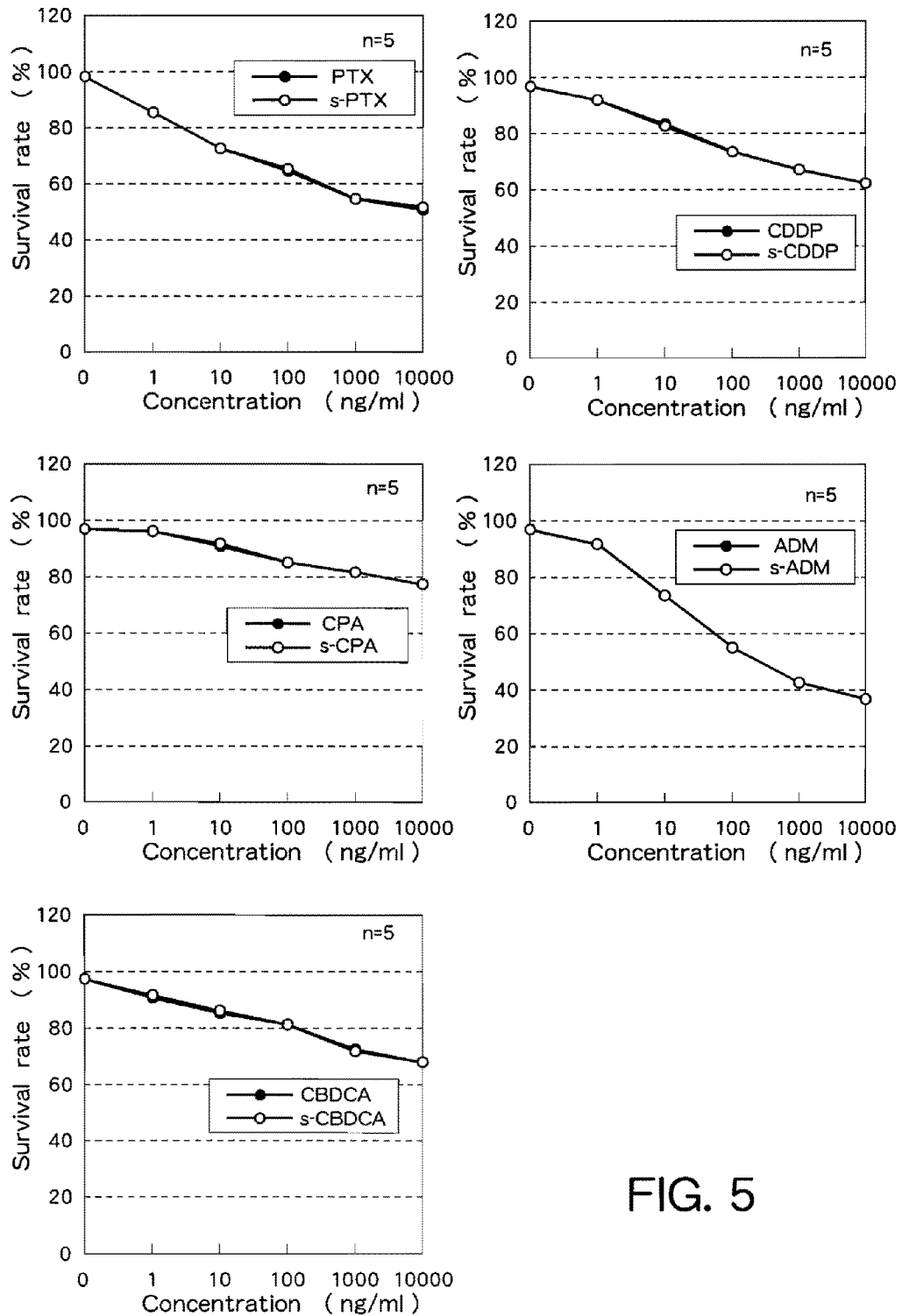
FIG. 5 shows graphs, each of which indicates a relationship between the concentration (ng/ml) of an added anticancer agent and the survival rate (%) of cells after 15 hours in Comparative Example 5.

The percentage of incorporation of a dye was counted 15 hours after adding an anticancer agent (s-PTX, s-CDDP, s-CBDCA, s-ADM, s-CPA, PTX, CDDP, CBDCA, ADM, or CPA) to confluent cells (stomach cancer cells) in the same manner as in Example 7 or Comparative Example 1, except that stomach cancer cells were used as the cells in place of NUTOS. The results are shown in FIG. 5.

As is apparent from the comparison between FIGS. 1 and 2 and FIGS. 3, 4, and 5, the serotonin-anticancer substance conjugate medicinal agents (s-PTX, s-CDDP, s-CBDCA, s-ADM, and s-CPA) synthesized in Examples 2 to 6 exhibited an anticancer effect specifically on alveolar rhabdomyosarcoma obtained from the tongue and alveolar rhabdomyosarcoma obtained from the mammary gland. This is considered to be because the serotonin-anticancer substance conjugate medicinal agents are specifically incorporated into a rhabdomyosarcoma. On the other hand, endometrial cancer, ovarian cancer, and stomach cancer hardly incorporate the serotonin-anticancer substance conjugate medicinal agents, and therefore, the serotonin-anticancer substance conjugate medicinal agents (s-PTX, s-CDDP, s-CBDCA, s-ADM, and s-CPA) synthesized in Examples 2 to 6 did not exhibit an anticancer effect on endometrial cancer, ovarian cancer, and stomach cancer.

As described above, by binding an acting substance (anticancer substance) that can act on the function of a target cell (rhabdomyosarcoma) to a cell-incorporated substance (serotonin) that can specifically be incorporated into the target cell (rhabdomyosarcoma), a medicinal agent for medical applications that can specifically act on the function of the target cell (rhabdomyosarcoma) was obtained. This medicinal agent for medical applications can be applied to a drug delivery system (DDS) and the like.

Further, by selecting serotonin as a cell-incorporated substance that can specifically be incorporated into a target cell (rhabdomyosarcoma) and binding an acting substance (anticancer substance) that can act on the function of the target cell (rhabdomyosarcoma) to the selected cell-incorporated substance (serotonin) so as to obtain a cell-incorporated substance-acting substance conjugate medicinal agent, a novel medicinal agent that can specifically act on the function of a target cell (rhabdomyosarcoma) was successfully searched for by a simple method.

The invention claimed is:

1. A medicinal agent for medical applications, comprising: serotonin conjugated with an anticancer substance for a rhabdomyosarcoma, wherein said anticancer substance is selected from the group consisting of paclitaxel, cisplatin, carboplatin, doxorubicin and cyclophosphamide.

2. The medicinal agent for medical applications according to claim 1, wherein the anticancer substance is paclitaxel.

3. The medicinal agent for medical applications according to claim 1, wherein the anticancer substance is cisplatin.

4. The medicinal agent for medical applications according to claim 1, wherein the anticancer substance is carboplatin.

5. The medicinal agent for medical applications according to claim 1, wherein the anticancer substance is doxorubicin.

6. The medicinal agent for medical applications according to claim 1, wherein the anticancer substance is cyclophosphamide.

* * * * *